United States Patent [19]

Packard et al.

[11] Patent Number: 5,324,471
[45] Date of Patent: Jun. 28, 1994

[54] METHOD OF FORMING A MOLDED ARTICLE USING A MOLD HAVING AN ELASTOMERIC MOLD MEMBER

[75] Inventors: Thomas J. Packard, Somerset, Wis.; James H. Quackenbush, Eden Prairie, Minn.

[73] Assignee: Minnesota Mining and Manufacturing Company, St. Paul, Minn.

[21] Appl. No.: 737,175

[22] Filed: Jul. 29, 1991

Related U.S. Application Data

[62] Division of Ser. No. 360,473, Jun. 2, 1989, Pat. No. 5,111,904.

[51] Int. Cl.⁵ .................. B29C 41/14; B29C 41/20; B29C 41/42
[52] U.S. Cl. .................. 264/279; 264/279.1; 264/301; 264/313; 264/334
[58] Field of Search .............. 264/301, 305, 310, 311, 264/313, 337, 279.1, 279, 334

[56] References Cited

U.S. PATENT DOCUMENTS

| | | |
|---|---|---|
| 748,996 | 1/1904 | Spencer . |
| 1,682,691 | 8/1928 | Temple . |
| 2,310,362 | 2/1943 | Frissell . |
| 2,330,330 | 9/1943 | Beal et al. ............ 264/301 X |
| 2,338,827 | 1/1944 | Teague et al. ........ 264/305 X |
| 2,670,502 | 3/1954 | Cox ...................... 264/305 X |
| 2,709,279 | 5/1955 | Raiche . |
| 2,966,701 | 1/1961 | Heller .................. 264/255 X |
| 2,966,703 | 1/1961 | Harman ............... 264/255 |
| 3,020,669 | 2/1962 | Beyer-Olsen et al. ... 43/43.1 |
| 3,040,384 | 6/1962 | Whittington .......... 264/310 |
| 3,081,493 | 3/1963 | Beyer-Olsen et al. ... 264/310 X |
| 3,108,652 | 10/1963 | Littmann .............. 181/131 |
| 3,152,659 | 10/1964 | Littmann .............. 181/131 |
| 3,160,691 | 12/1964 | Chupa .................. 264/310 |
| 3,168,160 | 2/1965 | Littmann et al. ..... 181/131 |
| 3,168,161 | 2/1965 | Littmann .............. 181/131 |
| 3,204,959 | 9/1965 | Nicholls ............... 264/310 X |
| 3,275,099 | 9/1966 | Speelman ............. 181/131 |
| 3,288,901 | 11/1966 | Clark .................... 264/279.1 X |
| 3,295,631 | 1/1967 | Machlup .............. 181/131 |
| 3,437,172 | 4/1969 | Allen .................... 181/131 |
| 3,504,760 | 4/1970 | Littmann .............. 181/131 |
| 3,520,534 | 7/1970 | Bennett et al. ....... 264/311 X |
| 3,772,478 | 11/1973 | McCabe et al. ...... 181/131 |
| 3,899,044 | 12/1975 | Stumpf et al. ........ 181/135 |
| 3,906,071 | 9/1975 | Cook et al. ........... 264/305 X |
| 3,993,161 | 11/1976 | Shore ................... 181/135 |
| 4,011,925 | 3/1977 | French et al. ........ 181/131 |
| 4,029,169 | 6/1977 | Huntress .............. 181/135 |
| 4,094,688 | 6/1978 | Wolf .................... 106/38.2 |
| 4,200,169 | 4/1980 | MacDonald, III et al. ... 181/131 |
| 4,270,627 | 6/1981 | Hill ...................... 181/131 |
| 4,347,911 | 9/1982 | Bertagna et al. ..... 181/130 |
| 4,387,784 | 6/1983 | Hill ...................... 181/131 |
| 4,874,373 | 10/1989 | Luther et al. ......... 604/164 |
| 4,943,225 | 7/1990 | Prater .................. 264/305 X |

FOREIGN PATENT DOCUMENTS 38137 3/1983 Japan .

OTHER PUBLICATIONS

Minnesota Mining & Manufacturing Company, "Fluorel ®" Fluoroelastomers Booklet Containing Inserts Published Between 1982 and 1987.
Minnesota Mining & Manufacturing Company, "The New Littmann ® Classic II Stethoscope" sales card published on or about Feb. 1984.

*Primary Examiner*—Karen Aftergut
*Attorney, Agent, or Firm*—Gary L. Griswold; Walter N. Kirn; John H. Hornickel

[57] ABSTRACT

A method for molding an article by dip or slush molding. The method includes the step of providing a flexible, heat resistant mold member. The mold member maintains its structural integrity during further heating and curing steps. Thus the mold member may therefore be used as an insert in the article to provide flexible stability at specific locations within the article. The mold member is made of a material which is substantially non-reactive with the molded article. The article may be any article made from a plastisol; in particular it can be a binaural for a stethoscope having a single or double lumens.

10 Claims, 2 Drawing Sheets

METHOD OF FORMING A MOLDED ARTICLE USING A MOLD HAVING AN ELASTOMERIC MOLD MEMBER

This is a division of application No. 07/360,473 filed Jun. 2, 1989, now U.S. Pat. No. 5,111,904.

FIELD OF THE INVENTION

The present invention relates to the use of molds made of a flexible, elastomeric material and used in the manufacture of molded articles, such as stethoscopes. The flexible, elastomeric molds may optionally be connected to other portions of a mold during the manufacturing process, but may be separated from such other portions after molding to remain in the molded article.

BACKGROUND OF THE INVENTION

Special problems are presented in the manufacturing process of molded articles, which are intended to have internal bores, cavities, or voids. The bores, cavities, or voids of the completed molded article may be filled with other structural components such as springs, connector bushings, and the like. The dimensions of the internal cavities must be established and maintained during the manufacturing process, in order that such inserts may be properly assembled later.

Even more difficult is the manufacturing process where the internal cavities are intended to transmit sound, air, or other fluids where the internal dimensions of the cavities are critical to the properties of the fluids moving therethrough.

The manufacture of molded articles having internal cavities such as stethoscopes accentuate the difficulties of manufacturing because the sound passages must have certain acoustical qualities in order to permit the physician to accurately hear the condition of the patient under examination.

The acoustical passages of the stethoscope, the lumens, may transmit the sound from the patient to one ear of the physician, called a monaural tubing, or to both ears of the physician, called a binaural tubing. The sound passages in the stethoscope may have a common internal cavity, or single lumen, from the patient to the yoke of the stethoscope, whereupon the single lumen divides into two passages, one for each ear of the physician.

Alternately, the stethoscope may have double lumens from the microphone placed against the patient to the yoke of the stethoscope, whereupon the pair of lumens divide, one to each ear of the physician.

As can be appreciated by those skilled in the art, the molding of a long, narrow object, having at least one, and preferably two, internal passageways presents considerable manufacturing difficulties where the acoustical quality of the stethoscope is directly dependent upon the structural configuration of the lumens between the microphone and the ear of the physician. In this regard, U.S. Pat. No. 4,200,169 discusses the importance of the configuration of internal binaural lumen passages and the resolution of acoustical quality in the stethoscope of that invention by the substantial maintenance of a constant diameter throughout the lumens.

Often, stethoscopes are manufactured using the process of hot dip molding. A mold is assembled, heated, and dipped into a liquid plastic or plastisol to permit the plastisol to contact all surfaces of the mold. The amount of plastisol which gels around the mold is related to the heat of the mold when it enters the plastisol reservoir. The mold is withdrawn from the plastisol reservoir and is heated to cure the plastisol into the plastic article comprising the binaural tubing of the stethoscope. The segments of the mold are removed, leaving the internal passages, or lumens, within the binaural tubing. The other components of the stethoscope are attached to the binaural to complete the manufacture of the stethoscope.

Some portions of the mold may require additional thickness of the plastisol in order to provide greater structural stability of the article after molding during usage by the physician. The yoke of the stethoscope, where the lumens separate and are directed to each ear, is a particularly vulnerable portion of the stethoscope during the stress and strain of usage. And the yoke portion of the mold must counteract the force of gravity during the manufacturing process as the plastisol flows on the mold as the mold moves from one area of manufacture to the next. Therefore, that portion of a dip-molding form is subjected to direct, additional heating to achieve additional gelation of the plastisol about that portion of the form to counteract plastisol flow and reinforce a critical junction of the molded article.

The additional steps of direct heating of critical portions of the form to provide additional wall thickness for the molded article is known as the process of "building". Thus, when stethoscopes are manufactured using hot dip molding, it is necessary in the molding of the binaural tubing to "build" sufficient wall thickness at critical portions of the binaural tubing without compromising the desired acoustical quality of the binaural lumens being formed therein.

Currently, as known to those skilled in the art, whenever sufficient wall thickness must be "built", the mold is placed before an open flame in the specific area of the mold requiring "building". Use of an open flame in a manufacturing process is an inexact method at best, even for "build" formation. Atmospheric or climatic conditions, temperature of the flame, and subjective opinions of the manufacturer establishing the processing conditions for the open flame "building" all result in an unpredictible and potentially non-replicating manufacturing process step for the formation of a stethoscope which demands replicated acoustical qualities. Further, the presence of open flames in manufacturing processes represents a potential dangerous manufacturing condition in the presence of any combustible materials or gases.

Molds intended for complete removal after a hot dip molding process are typically made entirely of a material capable of withstanding the temperatures of preheating, including "build" temperatures during preheating, and curing. However, unfortunately, such heat resistant materials are also rigid and not nearly as flexible as the article molded from the plastisol.

In the case of stethoscopes, the entire length of the binaural tubing must have sufficient flexibility to facilitate use by the health care practitioner. In other words, the molded stethoscope must be flexible along the entire length of its tubing to permit comfortable placement about the head of the health care practitioner and to flex at various locations in order to reach that portion of the body of the patient requiring examination.

If it were desired to avoid the use of an open flame in order to "build" wall thickness at portions of a stethoscope subject to stress and strain during usage, the only molds available to those skilled in the art are heat resistant materials which are rigid and not nearly as flexible as the article to be molded from the plastisol.

Thus, if the rigid mold were left in the stethoscope, after molding was complete, that rigid mold or mold segment would severely interfere with the flexibility and proper use of the stethoscope. Moreover, where a rigid mold or a mold segment is left in the stethoscope, the yoke junction of the stethoscope where the lumens divide would be subject to undesirable pressure and movement as the yoke is flexed.

Hence, what is needed in the art is a method for molding articles which eliminates any necessity of open flame "building" along those portions of the articles which require flexible yet stable junctions, like the yoke portion of the stethoscope. The art also needs a mold which has a member which is both heat resistant and flexible which optionally may remain embedded in the molded article after molding to augment the stability of the molded article at the critical junction, obviating the need for open flame "building" of additional wall thickness.

SUMMARY OF THE INVENTION

The present invention solves the problem of the prior art by providing a mold which is both flexible and heat resistant. The use of such flexible, heat resistant mold eliminates the necessity of "building" because the stability provided by "building" the extra wall thickness at a critical junction is now optionally replaced by the mold member remaining in the molded article after the molding process is complete. Since the mold member is both flexible and capable of withstanding the effects of preheating and curing heat without diminished structural integrity, it may be retained in the article after molding.

Therefore, the molded member of the present invention is stable and compatible with the cured plastisol and augments the strength of that cured plastisol at critical junctions of the molded article, such as the yoke junction of a stethoscope.

The present invention also provides the use of the flexible, heat resistant mold member in conjunction with at least a more rigid portion of a mold, which is separable from but connectible with such mold member through pivoting of the rigid portion of the mold about a hinge, in order to facilitate removal of the rigid portion of the mold while retaining the flexible member in the molded article.

The present invention also provides for the method of manufacture of a molded article by molding a plastisol about a mold having a heat resistant, flexible member whereby the member may optionally remain in the molded article to provide flexible structural strength at critical junctions in the molded article.

The present invention also provides a molded article formed by molding a plastisol about a mold having a heat resistant, flexible member whereby the member becomes a structural component of the molded article to provide structural strength at critical locations in the article without reacting with the article and without sacrificing flexibility of the article.

These and other objects of the present invention will become apparent in view of the following description of the invention and the preferred embodiments.

DESCRIPTION OF THE DRAWINGS

Further understanding the invention will be facilitated by reference to the encompanying drawings wherein.

DETAILED DESCRIPTION OF THE PREFERRED EMBODIMENTS

The present invention may be used to make a wide variety of molded articles which may have internal cavities, bores, or voids therein, either for positioning other components therein, (such as springs or the like) or for transmitting sound, maintaining air or gasses, or moving or storing liquids. By way of example, not by way of limitation, the variety of such molded articles may include traffic cones, fishing buoys or markers, industrial cable sheathing, and the like.

The present invention has particular utility in making stethoscopes and thus the following detailed description describes stethoscopes. However, the invention is not limited to stethoscopes, or the particular alternate constructions of stethoscopes. For example, the stethoscope may have monaural or binaural tubing or may have either single or double lumens as passageways without the departing from the scope of this invention.

Figure 1:
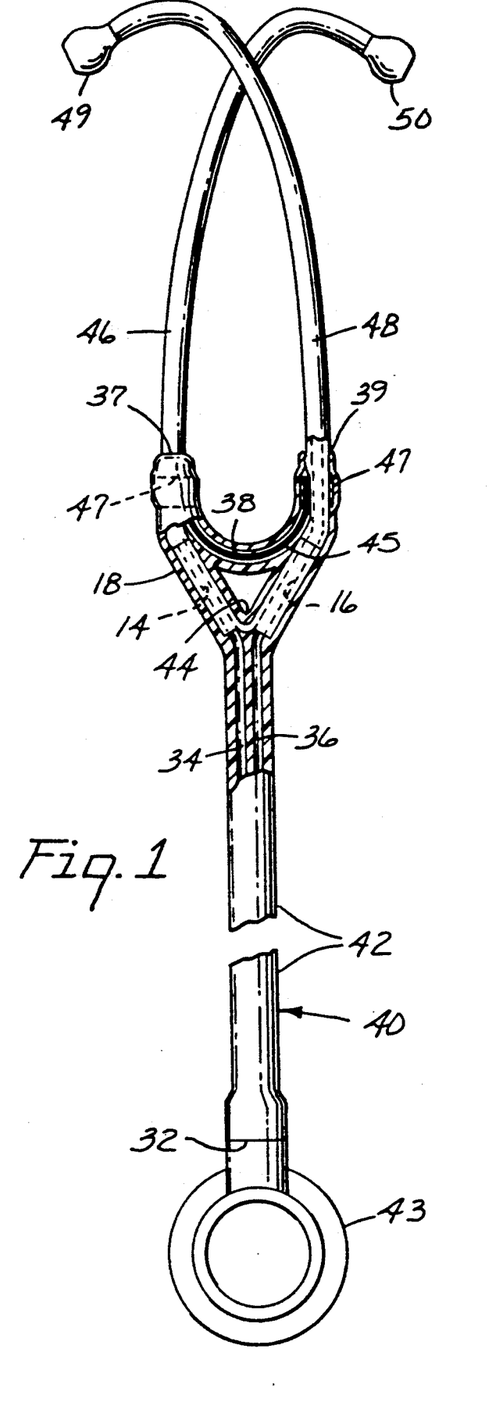
FIG. 1 is a partial cut-away view of one of the preferred embodiments of a stethoscope having the flexible, heat resistant member molded therein at the yoke junction of the stethoscope.

Referring to FIG. 1, a molded article 40 is illustrated, which is a stethoscope within the scope of the present invention having in one preferred embodiment a flexible, heat resistant member 18 embedded therein at a yoke junction 44 of a binaural 42 having double lumens 34 and 36 terminating in a bottom edge 32.

Figure 2:
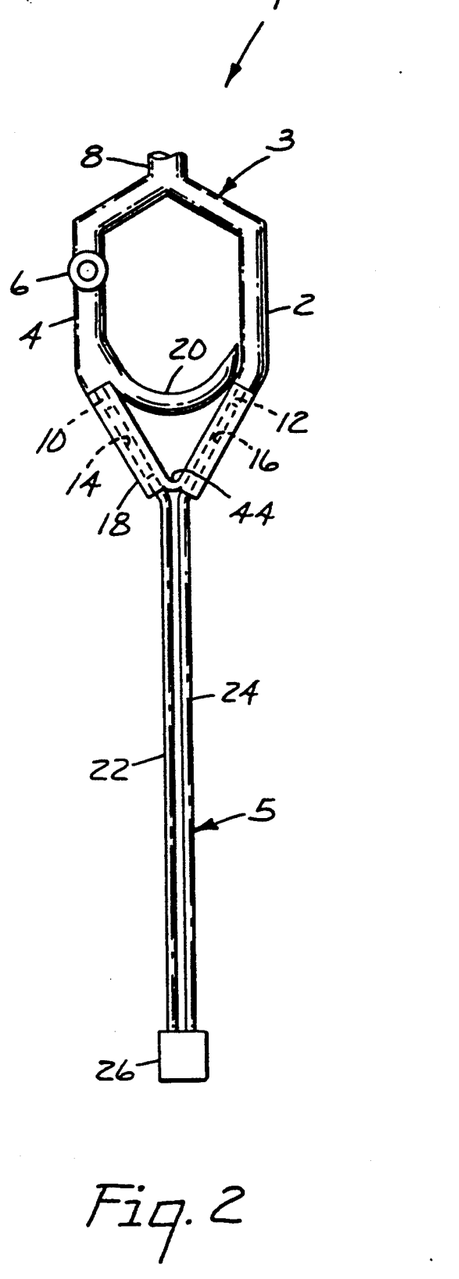
FIG. 2 is one of the preferred embodiments of a dip molding form prior to commencing the molding operation.
Figure 3:
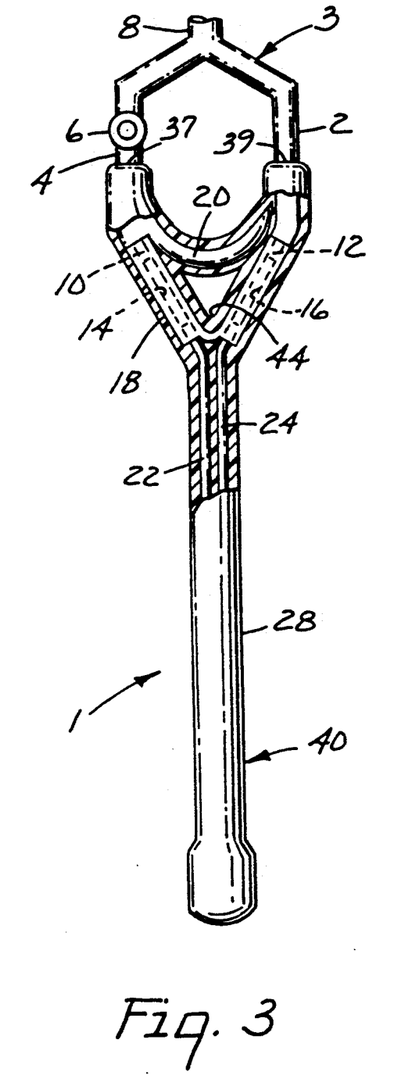
FIG. 3 is a partial cut-away view of the dip molding form of FIG. 2 coated with the cured plastic material before demolding.
Figure 4:
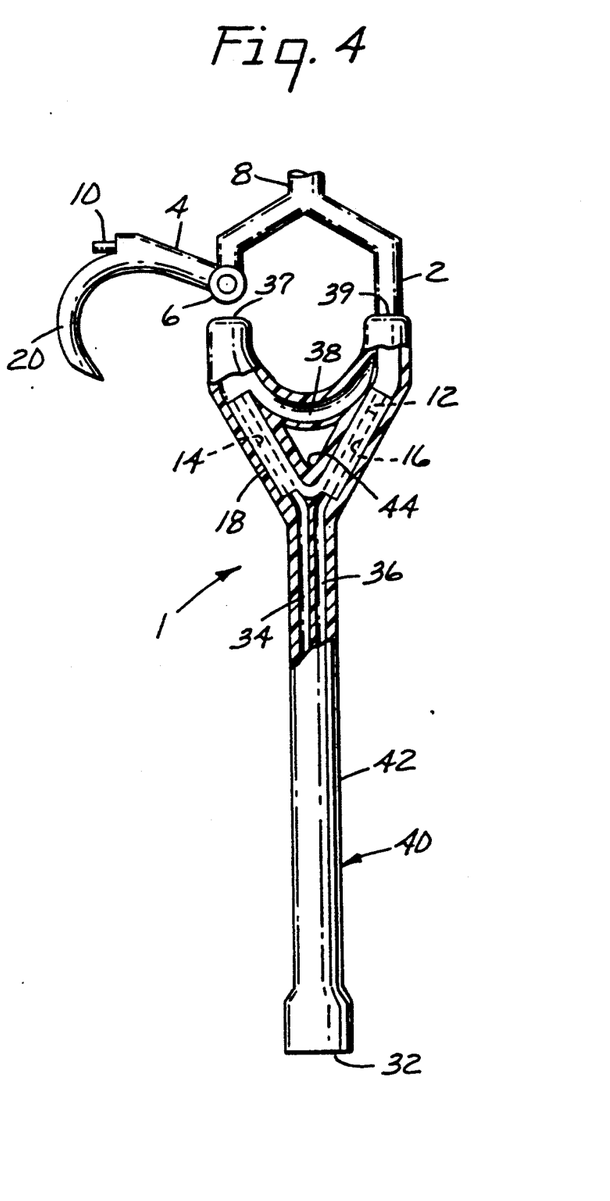
FIG. 4 is a partial cut-away view of the dip molding form of FIG. 2 during the process of demolding.

In this preferred embodiment, member 18 has optionally remained embedded in the article 40 after completion of the molding and demolding processes as seen through the progression of FIGS. 2-4. However, it is within the scope of the present invention to provide a molded article having any shape of internal cavity or bore which matches the shape of the removable portion of the mold or matches the shape of the optionally removable member 18.

For example, a leaf spring cavity 38, cavities for ear tubes 46 and 48, and lumen cavities 34 and 36 match the shape of the removable portions of a mold, whereas the cavity at yoke junction 44 matches the shape of the member 18 optionally remaining in the article 40 after demolding of the separable portions of the mold.

FIG. 2 illustrates a molding form 1 having flexible, heat resistant member 18 connected to a more rigid upper portion 3 and a more rigid lower portion 5.

The more rigid upper portion 3 has a fixed upper portion 2, a pivoting upper portion 4, and a mold support portion 8. Pivoting upper portion 4 has a hinge portion 6 to facilitate rotation of a leaf spring mold portion 20 from the molded article 40 during demolding. More rigid upper portion 3 may be made of metal, and preferably may be made of stainless steel.

More rigid lower portion 5 has two optionally removable lower portions 22 and 24 terminating in a fitting 26. More rigid lower portion may be made of metal, and preferably may be made of stainless steel.

Portions 22 and 24 represent the mold segments by which double lumens 34 and 36 in the molded article 40 may be made. However, as stated above, it is within the scope of the present invention to provide either a single or double lumen sound passageway. If a single lumen passageway is desired, either of portions 22 or 24 may be eliminated.

Member 18 has an internal bore 14 and an internal bore 16 which presently, preferably, have constant diameters of equal dimension.

Relatively rigid upper portion 3 and relatively rigid lower portion 5 may be connected with member 18 to assemble a molding form 1 in order to make a stethoscope of a preferred embodiment of the present invention. Fixed upper portion 2 has a protrusion 12, and pivoting upper portion 4 has a protrusion 10 which are removably inserted into internal bores 16 and 14, respectively of member 18. Likewise, the terminii of lower portions 22 and 24 opposite fitting 26 are inserted into the opposite end of internal bores 14 and 16, respectively, of member 18. Molding form 1 is thereby assembled.

The molding form 1, as shown in FIG. 2, is consistent with the teachings of U.S. Pat. No. 4,200,169 to provide a stethoscope having excellent acoustical integrity. The relative dimensions of the various portions of the molding form 1 are configured in such a way as to have a substantially constant diameter for the binaural tubing 42 after the removable portions 3 and 5 of the molding form are removed. In order to achieve such substantially constant diameter, the diameter of protrusions 10 and 12 are preferably the same as the diameter of removable lower portions 22 and 24. The internal diameter of bores 14 and 16 of member 18 are also preferably substantially the same diameter as protrusions 10 and 12 and portions 22 and 24.

Specifically, as seen in FIG. 2, bore 14 has the same diameter as protrusion 10 and lower portion 22. Bore 16 has the same diameter as protrusion 12 and lower portion 24. This substantial identity of diameters is also important to assure a well fitting form 1, which will not dissemble prematurely during the manufacturing process.

Member 18 must be at least as flexible as upper portion 3 and lower portion 5 to be useful in accordance with the present invention. Preferably, member 18 is more flexible than portions 3 and 5 of mold form 1. The usefulness of member 18 in accordance with the present invention is a function of its flexibility in relation to the article 40 to be made.

The flexibility of member 18 is a relative condition determined by the chemical composition of article 40 and the composition of member 18. Flexibility or resiliency is a concept measured according to the scope of this invention as a lack of hardness, which is a standard of materials measurement. The standard to which the present invention refers is ASTM Standard D2240, which results in measurement along the Shore scales of hardness.

In the case of the present invention, the Shore A scale of hardness is used. It is within the scope of the present invention to provide a member 18 to be composed of a material having a flexibility generally compatible with the flexibility of the desired molded article. In other words, depending upon the flexibility property for the molded article 40 desired, the flexibility of the member 18 may be greater or less than the flexibility of the molded article 40.

Desirably, flexibility compatability may be achieved when the member 18 has a flexibility slightly greater than, equal to, or slightly less than the flexibility of the molded article 40.

In the case of a preferred embodiment of the molded article 40 being a stethoscope made of a plastisol cured into an elastomer, the member 18 is desirably made of an elastomeric material having a Shore A hardness of from about 5 Shore A to about 95 Shore A, within which range exists materials which could also have the desired heat resistance properties within the scope of the present invention. An elastomeric material having a Shore A hardness less than 5 Shore A would yield a member too flexible and soft to provide stability for the molded article at critical locations such as yoke junction 44 of article 40 because such materials lack the heat resistance capable of withstanding the manufacturing process to maintain structural integrity. A member 18 made of elastomeric material having a Shore A hardness greater than 95 Shore A would be too hard and stiff to yield a truly flexible material even though providing suitable heat resistance during the manufacturing process.

Preferably, the insert 18 is made of an elastomeric material having a Shore A hardness of from about 20 Shore A to about 80 Shore A, within which range members formed to have internal cavities such as acoustical bores, in order to maintain sufficient structural integrity of the member 18 during the manufacturing process and thereafter during usage of the article 40.

Optimally, for a binaural tubing for a stethoscope made from a plastisol such as that disclosed in Example 1 of U.S. Pat. No. 4,200,169, which patent is incorporated herein by reference, the member 18 has a Shore A hardness of from about 30 Shore A to about 50 Shore A. This range of hardness, (or depending on ones perspective, flexibility), closely approximates the Shore A hardness of cured plastics made from the dip molding of plastisols for use as stethoscopes.

While member 18 must be compatibly flexible during the manufacturing process and during subsequent usage of the article 40 if the member 18 remains therein after manufacturing, in any event, the member 18 must be heat resistant during the manufacturing process. By resisting heat, member 18 retains sufficient structural integrity during the manufacturing process.

If the member 18 is to remain optionally embedded in the article 40 for use as a stethoscope, member 18 cannot disrupt the acoustical quality of the binaural 42 but can add to the stability of the article 40 at yoke junction 44. That added stability to the yoke junction obviates the necessity of open flame "building" during the manufacturing process to achieve additional wall thickness at yoke junction 44. The heat resistance of member 18 does not alter its flexibility described above.

Thus, the flexibility of member 18 at yoke junction 44 provides stability without disrupting the flexibility of the article 40 at junction 44 and without disrupting the acoustical quality of the article 40 through sound passageways 34 and 36.

The extent of heat resistance of the member 18 is dependent upon exposure to two separate heating conditions during the molding process of the present invention.

The molding form 1 is often pre-heated for its short duration when a particularly thick coat of plastisol is to be molded about it. The pre-heating temperature ranges sometimes as high as 290° C., and usually as high as between 260° C. and 275° C.

During the curing process of the article 40 formation, the molding form 1 including member 18 is exposed during the curing process through the plastisol surrounding it to temperatures ranging from about 175° C. to about 205° C.

Therefore, the member 18 as a part of molding form 1 or alone as the entire mold itself, is exposed to the process steps of pre-heating and curing. The flexible member 18 must be capable of resisting direct and indirect exposure to heat in a range of from 175° C. to about 290° C. The member 18 desirably must be capable of resisting loss of structural integrity at temperatures ranging from 190° C. to about 275° C. Preferably, the member 18 used as a portion of a molding form 1 to manufacture tubing for a stethoscope of the present invention must be capable of resisting temperatures of from about 190° C. to about 260° C. Plastisols requiring "building" for molding into tubing for stethoscopes typically require curing temperatures of this range.

In addition to flexibility compatability described above, member 18 should also be compatible with the physical and chemical properties of the plastisol during and after molded formation into article 40. This is particularly true if member 18 optionally is to remain embedded in the article 40.

In other words, the member 18 should not react with the chemical composition of the plastisol nor should there be rapid degradation of the structural integrity of the member 18 during and after the molding process. Degradation of the structural integrity of the member 18 would weaken the member 18 at yoke junction 44 which would reduce the flexible stability provided at that critical location of article 40. Also, the degradation of structural integrity of member 18 would alter the acoustical qualities of the binaural 42.

Chemical or physical incompatibility with the article 40 could immediately or gradually alter the usefulness of article 40 as an instrument for consistent diagnosis.

For member 18 to be embedded in article 40, the non-reactivity of the member 18 should be at least longer than the projected useful life of the article 40. In other plastisol compatibility decisions, a short duration elevated temperature test may predict possible long term stability. Example 2 below describes such a test for a preferred embodiment of the article 40 of the present invention.

Thus, it is important to the present invention to have a member 18 which is flexible, heat resistant, and non-reactive with the article 40 and the plastisol from which it is made. Therefore, member 18 may be composed of any flexible, heat resistant material which will be non-reactive with the chemical composition of the article 40, particularly when that member 18 is to remain embedded in the article 4.0 after molding and demolding.

For a member 18 useful with a plastisol such as that disclosed in Example 1 of U.S. Pat. No. 4,200,169, an elastomeric material is preferred in the formation of flexible components for a stethoscope.

Generally, acceptable elastomeric materials for member 18 include fluorocarbon elastomers. Within the group of fluorocarbon elastomers, desirably for the present invention, a fluorocarbon elastomer comprising an oligomer comprising vinylidene fluoride and at least one fully fluoro substituted olefin having less than four carbon atoms may be used.

Examples of such fluorocarbon elastomers having a copolymer or terpolymer of vinylidene fluoride and at least one fully fluoro substituted olefin having less than four carbon atoms are poly(vinylidene fluoride-co-hexafluoropropylene) available from Daikin under the brand "Dai-el", available from Minnesota Mining and Manufacturing Company under the brand "Fluorel", available from Montedison under the brand "Tecnoflon", available from DuPont under the brand "Viton"; poly(vinylidene fluoride-co-hexafluoropropylene-co-tetrafluoroethylene) available from Daikin under the brand "Dai-el", available from Minnesota Mining and Manufacturing Company under the brand "Fluorel", available from Montedison under the brand "Tecnoflon", available from DuPont under the brand "Viton"; poly[vinylidene fluoride-co-tetrafluoroethylene-co-perfluoro(methyl vinyl ether)] available from DuPont under the brand "Viton"*; and poly[tetrafluoroethylene-co-perfluoro (methyl vinyl ether)] available from DuPont under the brand "Kalrez". Other fluorocarbon elastomers useful for this invention include poly(tetrafluoroethylene-co-propylene) available from Asahi Glass under the brand "Aflas"*; and poly(vinylidene fluoride-co-chlorotrifluoroethylene) available from Minnesota Mining and Manufacturing Company under the brand "Kel-F"*. Reference in this paragraph to fluorocarbon elastomers using the symbol * indicates such elastomers are peroxide-curable.

Of these fluorocarbon elastomeric materials, poly(vinylidene fluoride-co-hexafluoropropylene) is preferred. That compound is available from the Minnesota Mining and Manufacturing Company of St. Paul, Minn. in several grades. Preferably for the present invention, member 18 may be made from grade FC2174 Fluorel TM. Alternately, for member 18, grade FLS2690 Fluorel TM may also be used.

A member 18 of the present invention having heat resistance, flexibility, and non-reactivity may be useful in the formation of any article which is capable of being molded using a removable mold, (whether or not having bores, cavities, or voids contained therein), and optionally having a portion of the mold remain in the article after formation.

Formation of molded articles using dip molding or slush or rotational (3-axis) molding techniques may be utilized with the methods of the present invention to achieve elastomeric or polymeric articles having a variety of utilities.

For the technique known as dip molding, generally it is known to those skilled in the art to provide a plastisol such as that disclosed in Example 1 of U.S. Pat. No. 4,200,169. Plastisols typically include polymer forming resins (often having residues of emulsifiers contained therein), plasticizers, stabilizers, cross-linking agents, thixotropic agents, and pigments. Examples of typical ranges of concentrations of the components of the plastisols are identified in Table 1 below.

As is known to those skilled in the art of plastisol molding processes, no single plastisol processing composition or molding process is universally applicable. Rather, there are many variables in selection and use of the plastisols.

The intended use of the final article molded from the plastisol also requires careful selection of the components which are not toxic or odorous or otherwise undesired by the user of the molded article. Environmental or ergonomic considerations must be given to the end use of the article.

Therefore, it is within the scope of the present invention to contemplate several plastisol formulations for a variety of useful articles depending upon such variables and factors, without departing from the desirability of the present invention to retain member 18 embedded in the article 40 after the molding process is completed.

More extensive discussions concerning the art of plastisol formulation for a variety of useful articles include Sarvetnick, H. A. *Plastisols and Organisols*, Van Nostrand Reinhold Co., 1972 and Chevassus, F. and Broutelles, R., *The Stabilization of Polyvinyl Chloride*, St. Martins Press, Inc., 1963, which references are incorporated herein as if rewritten.

In the case of the present invention, the polymer resin may comprise homopolymers of polyhaloolefins, (such as polyvinyl chloride) or copolymers of polyolefins (such as polyvinyl chloride and vinyl acetate). Preferably, the plastisol used in the present invention is based on a polyvinyl chloride dispersion resin, suspended in a high solvating plasticizer, with a strong heat stabilizer provided.

While many plastisol formulations known to those skilled in the art for a variety of useful plastisol molded articles may be used within the scope of the present invention, desirably, the following table identifies suitable ranges of plastisol components for the formation of dip-molded articles.

TABLE I

| COMPONENT | PARTS BY WEIGHT/ 100 PARTS OF RESIN |
| --- | --- |
| High Molecular Weight Polyvinyl Chloride Homopolymer Resin | 100 |
| Butyl Benzyl Phthlate Plasticizer | 60–70 |
| Dialkyl Phthlate Plasticizer | 15–25 |
| Epoxidized Oils Synergist | 03–07 |
| Free Chloride Binding Heat Stabilizer | 02–05 |
| Pigment | 02–04 |

The plastisol mixed from the components in Table I, in any of the possible formulations, permits intimate contact with the molding form 1 to be coated. Thus, the coating plastisol can reach small shapes and recesses and can conform accurately to small changes in dimensions in the article to be coated.

The coating of the form 1 to form article 40 is particularly valuable when one wishes to encase an article with a material which will seal it efficiently from the outside. Thus, in the case of the present invention, a binaural tubing for a stethoscope molded using form 1 can achieve the acoustical qualities taught in U.S. Pat. No. 4,200,169 by forming an article 40 which has no structural interruptions throughout its length.

As discussed above, the invention is particularly suited to forming a binaural tubing 42 for a stethoscope. The binaural tubing 42 includes a v-shaped, heat resistant, elastomeric member 18 having internal bores 14 and 16, each one penetrating the length of each of the legs of member 18. Each of these bores will become part of one of the pair of substantially separate sound conduction paths through the binaural 42.

A coating of plastic is formed by dip molding in a plastisol, substantially surrounding the elastomeric member 18, and within this coating the uppermost portions of the two sound passages 34 and 36 are formed.

FIG. 2 shows how the molding form 1 is assembled. The removable upper portion 3 engages the flexible member 18 which engages the removable lower portion 5. The engagement occurs at opposing ends of bores 14 and 16 as previously described.

Molding form 1 is then heated to a dipping temperature, typically in an oven. Whereas in the prior art, an open flame was directed against the upper portion 3 including the v-shaped portion used to form the yoke, in order to "build" the plastisol at those portions; in the present invention no open flame is needed to provide sufficient thickness of plastisol.

After heating, form 1 is dipped into a tank of plastisol. Referring to FIG. 3, after the form 1 is withdrawn from the plastisol tank, a coating of curable plastic 28 gels around form 1. At least the member 18 and optionally other portions 3 and/or 5 of molding form 1 are now substantially surrounded by gelled, but uncured plastisol. Next, the gelled plastisol is cured, typically by heating in an oven, forming a solid, flexible plastic article 40.

Referring to FIG. 4, the removable portions 3 and 5 of molding form 1 are removed from the article 40, leaving the flexible, heat resistant, elastomeric member 18 at yoke junction 44 of the article 40, which is shown in FIG. 1.

Referring again to FIG. 4, the article 40 is being demolded. The lower most portion of the binaural tubing 42 (now cured from plastic coating 28 as seen in FIG. 3), leaving a bottom edge 32 for attachment of the chestpiece 43 (as seen in FIG. 1). The lower portions 22 and 24 of molding form 1 have been removed by pulling on the fitting 26 (not shown), leaving behind two sound conduction passages 34 and 36. The bore 14 in the heat resistant, flexible member 18 now forms part of the sound conduction pathway 34 and bore 16 now forms part of the sound conduction pathway 36.

Referring again to FIG. 4, the pivoting upper portion 4 has been freed from binaural tubing 42 by rotating it on its hinge 6. The cavity 38 will be occupied by leaf spring 45 (as seen in FIG. 1) when the stethoscope is assembled.

The finished article 40 will next be pulled downwards and off the fixed upper portion 2, completing the demolding sequence. Thereafter, the end of chestpiece 43 may be inserted into bottom edge 32. Leaf spring 45 may be inserted into cavity 38. Ear tubes 46 and 48 may be inserted into the uppermost ends 37 and 39 of binaural tubing 42 against bores 14 and 16, respectively, of member 18. Preferably, tubes 46 and 48 are interconnected with spring 45, by bushings 47, staked or welded about such connection location on tubes 46 and 48, as shown in FIG. 1 for one bushing 47. The spring-tube sub-assembly is assembled by placing one ear tube 48 into one uppermost end 37 of tubing 42, through spring cavity 38, and out the other uppermost end 39 of tubing 42. Ear tips 49 and 50 are then assembled on ear tubes 46 and 48, respectively. The sound conduction passages in ear tubes 46 and 48 register with the uppermost ends of bores 14 and 16 to achieve acoustical integrity. Preferably then, the lumens with ear tubes 46 and 48 have the same diameter as the bores 14 and 16 to achieve constant diameter acoustical integrity.

Consistent with the teachings of U.S. Pat. No. 4,200,169, the sound conduction passages 34 and 36 as extended by the bores 14 and 16, respectively, are substantially uniform throughout and constitute a continuous leak-free sound passage. This provides the desired acoustical integrity.

Furthermore, the presence of the heat resistant, elastomeric member 18 will provide sufficient stability and flexibility at the critical yoke junction 44 to obviate the need for unpredictable open flame "building" of wall thickness. The flexible stability provided by member 18 will resist deterioration of such junction 44 through pressure and movement at that location without disrupting the flexibility of the junction 44 by virtue of the member's own compatible flexibility.

Also, the retention of the member 18 embedded at junction 44 of article 40 helps provide a good aesthetic appearance, visually presenting a substantially even external thickness from top to bottom of the article 40 in spite of the tendency of the plastisol to drip downwards after the dipping step.

While it may be preferred to cause member 18 to remain embedded in the article 40 after molding and demolding are complete, it is within the scope of this invention to also remove member 18 from article 40 at the time of demolding. In that event, member 18 may be composed of two portions contacting each other in the area of the yoke junction 44 but fixedly secured to lower portion 5. When lower portion 5 is withdrawn from binaural tubing 42, the respective flexible member 18 portions may be concurrently withdrawn.

Alternately, the member 18 or its portions may be secured to one or more portions of upper portion 3 rather than lower portion 5 allowing withdrawal of member 18 or the portion which comprise it from the plastic coating 28 in a different direction.

Manufacture of articles 40 using slush or rotational (3-axis) molding processes is also within the scope of the present invention. For example, the slush molding process identified in U.S. Pat. No. 3,020,669 which is incorporated by reference herein may be adapted by one skilled in the art to employ the member 18 of the present invention in order to provide a molded article in which such member 18 remains embedded.

While not intended to be limited thereto or thereby, the following examples represent the usefulness of the present invention for a variety of useful dip-molded articles.

EXAMPLE 1

A dipping form according to FIG. 2 was fabricated using stainless steel for the support portion 8, both upper portions 2 and 4, both lower portions 22 and 24, and the fitting 26. Assembled with these permanent portions of the molding form 1 is a heat resistant, elastomeric member 18 fabricated by slicing partially through a 10.2 cm long, 0.338 cm I.D., 0.635 cm O.D. length of fluorocarbon tube commercially available from Minnesota Mining and Manufacturing Company under the Fluorel TM brand in the fluoroelastomer grade of FC2174. The overall length of the dipping form was about 53 cm. The molding form 1 was preheated in a forced air oven operated at 205° C. for a period of 8 minutes.

The preheated molding form 1 was slowly dipped into a pool of plastisol comprising 100 parts by weight of a polyvinyl chloride dispersion resin suspended in 60 parts by weight of butyl benzyl phthalate commercially available as Sanicizer 160 from Monsanto company of St. Louis, Mo., U.S.A. and 25 parts by weight of dialkyl phthlate available from Exxon Chemical of Houston, Tex., both serving as plasticizers. Five parts by weight of a free chloride binding heat stabilizer comprising a mixture fatty acid salt heat stabilizers available from Huls, of West Germany, and two parts by weight of carbon black disperion pigments available from Hatwick Chemical of Akron, Ohio were also present. After about 1.5 minutes, the dipping forms were withdrawn and allowed to drip into the pool briefly.

The molding form 1, now bearing a coating of gelled plastic 28, substantially as depicted in FIG. 3, was cured in a heated oven operated at between about 190° and 205° C. for about 6 minutes.

The finished article 40 was then stripped from the molding form 1. The lowermost portion of the plastic coating 28 was sliced away, exposing the fitting 26. The lower portions 22 and 24 were then removed by pulling on the fitting 26. The pivoting upper portion 4 was then freed from the binaural tubing 42 by rotating it on its hinge 6. This stage of the demolding was substantially as depicted in FIG. 4. The binaural tubing 42 was then pulled downwards and off of the fixed upper portion 2.

Leaf spring 45, and ear tubes 46 and 48 are then subassembled with bushings 47 and assembled through leaf spring cavity 38. Chestpiece 43 and ear tips 49 and 50 are passed into position to complete the assembly of the molded article 40 in a preferred embodiment of a stethoscope.

Referring again to FIG. 1, the binaural tubing 42 assembled as a stethoscope retains the flexible, heat resistant member 18 at the yoke junction 44 of the article 40 to provide "build" stability without sacrificing flexibility at the junction 44 during usage under a variety of movements by the health care practitioner and the patient during diagnosis.

The passageways 34 and 36 of binaural tubing 42 are substantially of the same diameter throughout including through bores 14 and 16 of member 18. The continuous binaural tubing 42 provides a leak-free acoustic environment for the sounds transmitted through the article 40. The embedment of member 18 is compatible with and non-reactive to the binaural tubing 42, and the member 18 provides flexible stability to the yoke junction 44 of the article 40.

EXAMPLE 2

The binaural tubing 42 of article 40 resulting from Example 1 was heated to a temperature of 65.5° C. continuously for a period of one week. Visual examination of the binaural tubing 42 after such elevated short-duration heat exposure demonstrated no deleteriously interaction between the member 18 and binaural tubing 42. It is believed that such a test portends non-reactivity of the member 18 within binaural tubing 42 for at least 3 years when such article 40 is used and stored under normal conditions and ambient temperatures.

EXAMPLE 3

The fabrication of an article 40 having binaural tubing 42 is performed as in Example 1 except that in formulating the plastisol, the stabilizer used is four parts by weight of di-octyl tin maleate commercially available from M&T Chemicals of Rahway, N.J., instead of the fatty acid slat type stablizer.

EXAMPLE 4

The fabrication of article 40 having binaural tubing 42 is performed as in Example 1 except that in the formulation of the plastisol, five parts by weight of epoxidized oil commercially available from Viking Chemical of Blooming Prairie, Minn., is also incorporated as an auxiliary plasticizer and stabilizer synergist.

The binaural tubing 42 produced according to Examples 3 and 4 demonstrate the possibility of the usefulness of the formulations generally identified in Table I with a flexible, elastomeric mold member. Many other types of articles 40 requiring cavities therein optionally retaining flexible, but stable reinforcing inserts therein may be made within the scope of the present invention.

While certain embodiments of the present invention have been described in detail herein and as shown in the accompanying Drawings, it will be evident that various further modifications are possible without departing from the scope of the invention.

What is claimed is:

1. A method for forming a molded article, comprising the steps of:
   (a) providing a mold comprising a mold member comprising a fluorocarbon elastomeric material;
   (b) heating said mold;
   (c) dipping said mold into a plastisol comprising a high solvating aromatic plasticizer so as to form a layer of gelled plastisol thereon; and
   (d) heating said mold and said layer of gelled plastisol to form said article;
   wherein said fluorocarbon elastomeric material of said mold member maintains structural integrity during both heating steps and wherein said fluorocarbon elastomeric material of said mold member remains embedded in said article after step (d).

2. The method according to claim 1, wherein said mold further comprises a portion which is separately connected to said mold member, said method further comprising after step (d) the step of separating said portion from said mold member and removing said portion from said article.

3. The method according to claim 1, wherein said fluorocarbon elastomeric material comprises an oligomer comprising vinylidene fluoride and at least one fully fluoro substituted olefin having less than four carbon atoms.

4. The method according to claim 3, wherein said fluorocarbon elastomeric material comprises a copolymer of vinylidene fluoride and hexafluoropropylene.

5. A method for forming a molded article, comprising the steps of:
   (a) providing a mold comprising a mold member comprising a fluorocarbon elastomeric material capable of maintaining structural integrity when exposed to a temperature above 175° C. and having a Shore A hardness between about 5 Shore A and about 95 Shore A;
   (b) heating said mold to a temperature above 175° C.;
   (c) dipping said mold into a plastisol comprising a high solvating aromatic plasticizer so as to form a layer of gelled plastisol thereon; and
   (d) heating said mold and said layer of gelled plastisol to form said article;
   wherein said fluorocarbon elastomeric material of said mold member maintains structural integrity during both heating steps and wherein said fluorocarbon elastomeric material of said mold member remains embedded in said article after step (d).

6. The method according to claim 5, wherein said fluorocarbon elastomeric material has a Shore A hardness between about 20 Shore A to about 80 Shore A.

7. The method according to claim 5, wherein said fluorocarbon elastomeric material has a Shore A hardness between about 30 Shore A to about 50 Shore A.

8. The method according to claim 5, wherein said mold further comprises a portion which is separately connected to said mold member, said method further comprising after step (d) the step of separating said portion from said mold member and removing said portion from said article.

9. The method according to claim 5, wherein said fluorocarbon elastomeric material comprises an oligomer comprising vinylidene fluoride and at least one fully fluoro substituted olefin having less than four carbon atoms.

10. The method according to claim 9, wherein said fluorocarbon elastomeric material comprises a copolymer of vinylidene fluoride and hexafluoropropylene.

* * * * *

UNITED STATES PATENT AND TRADEMARK OFFICE
CERTIFICATE OF CORRECTION

PATENT NO.: 5,324,471
DATED: June 28, 1994
INVENTOR(S): Packard et al.

It is certified that error appears in the above-identified patent and that said Letters Patent is hereby corrected as shown below:

At column 9, line 13, "polyolefins" should read -- polyhaloolefins --.

Signed and Sealed this

Twelfth Day of December, 1995

Attest:

BRUCE LEHMAN

Attesting Officer

Commissioner of Patents and Trademarks